US008411989B2

(12) United States Patent
Chiba

(10) Patent No.: US 8,411,989 B2
(45) Date of Patent: Apr. 2, 2013

(54) SPECTRAL CHARACTERISTIC CALCULATING DEVICE AND METHOD

(75) Inventor: Toru Chiba, Tokyo (JP)

(73) Assignee: Hoya Corporation, Tokyo (JP)

( * ) Notice: Subject to any disclaimer, the term of this patent is extended or adjusted under 35 U.S.C. 154(b) by 671 days.

(21) Appl. No.: 12/417,966

(22) Filed: Apr. 3, 2009

(65) Prior Publication Data

US 2009/0252406 A1 Oct. 8, 2009

(30) Foreign Application Priority Data

Apr. 4, 2008 (JP) .................................. 2008-097810

(51) Int. Cl.
*G06K 9/40* (2006.01)
(52) U.S. Cl. ........ 382/274; 382/128; 382/129; 382/130; 382/131; 382/133; 436/63; 436/64; 436/164; 436/172
(58) Field of Classification Search .................. 382/274, 382/128, 129, 130, 131, 133; 436/63, 64, 436/164, 172
See application file for complete search history.

(56) References Cited

U.S. PATENT DOCUMENTS

| 5,078,150 | A | 1/1992 | Hara et al. | |
|---|---|---|---|---|
| 2002/0007122 | A1* | 1/2002 | Kaufman et al. | 600/476 |
| 2005/0018226 | A1 | 1/2005 | Chiba | |
| 2005/0046883 | A1 | 3/2005 | Chiba | |
| 2006/0253036 | A1* | 11/2006 | Takeuchi et al. | 600/478 |
| 2008/0205721 | A1* | 8/2008 | Udupa et al. | 382/128 |

FOREIGN PATENT DOCUMENTS

| EP | 1880659 | 1/2008 |
|---|---|---|
| JP | 1-280448 | 11/1989 |
| JP | 2006-255323 | 9/2006 |
| JP | 2006-314629 | 11/2006 |

OTHER PUBLICATIONS

English language Abstract of JP 1-280448, Nov. 10, 1989.
English language Abstract of JP 2006-255323, Sep. 28, 2006.
English language Abstract of JP 2006-314629, Nov. 24, 2006.
Evaluation and Analysis of Digital Color Image, Chapter 10, Estimation of Spectral Reflectivity and Its Application, Yoichi Miyake, Tokyo University Publication, Feb. 25, 2000.

* cited by examiner

*Primary Examiner* — Mike Rahmjoo
(74) *Attorney, Agent, or Firm* — Greenblum & Bernstein, P.L.C.

(57) ABSTRACT

A spectral characteristic calculation device stores a plurality of conversion matrices used to calculate the spectral characteristic values based on brightness values of a digital color image, and a plurality of pieces of brightness value information respectively corresponding to a plurality of sample groups. The plurality of conversion matrices are generated based on the sample color image information contained in the plurality of sample groups, respectively. An evaluating unit is configured to evaluate similarity of brightness value information of the target data with respect to each of the plurality of pieces of brightness value information of the plurality of sample groups. A conversion matrix corresponding to the sample group that is evaluated to have the highest similarity is selected as the conversion matrix. Then, a calculating unit calculates the spectral characteristic values of the target data using the conversion matrix selected by the selecting unit.

6 Claims, 2 Drawing Sheets

SPECTRAL CHARACTERISTIC CALCULATING DEVICE AND METHOD

BACKGROUND OF THE INVENTION

1. Technical Field

The present invention relates to a spectral characteristic calculating device configured to calculate a spectral characteristic of an arbitrarily selected pixel of an image represented by digital image data obtained by electronic endoscopes.

2. Related Art

It has been known that a healthy area and an involved area exhibit different spectral characteristics. For example, an involved area has a greater reflection ratio than a healthy area for light having a predetermined wavelength range. Making use of the spectral characteristic, it is suggested a diagnostic method for judging whether a target area includes an involved portion or not based on the spectral characteristic of an endoscopic image of a human body cavity. According to the above diagnostic method, typically, a spectrometer is coupled to a fiber scope to obtain the spectral characteristic with respect an arbitrary portion of the target area of the human cavity. Alternatively, a fiber bundle is inserted through a treatment instrument channel of an endoscope, and the spectrometer is connected to the fiber bundle at the proximal side thereof.

As above, in a conventional technique, when the diagnosis is done based on measurement of spectral characteristics, it is necessary to use a spectrometer separately. As an alternative, there is suggested a method for evaluating the spectral characteristic without using the spectrometer. An example of such a method is disclosed in *Evaluation and Analysis of Digital Color Image, Chapter 10, Estimation of Spectral Reflectivity and Its Application, Yoichi Miyake, Tokyo University Publication*. In the above publication, an image of the human cavity is obtained and a spectral characteristic is calculated based on brightness information of an arbitrary pixel of the image represented by the image data.

Generally, an image data obtained by an electronic endoscope is represented by brightness values of three primary colors, RGB (Red, Green and Blue). A wavelength range of the R component is 550 nm-700 nm, a wavelength range of the G component is 450 nm-600 nm and a wavelength range of the B components is 300 nm-500 nm. As described above, each color components has a relatively wide wavelength width (i.e., 100 nm-150 nm). Meanwhile, what is required in the spectral diagnosis is a brightness (reflectivity) with respect to light having a relatively narrow range (e.g., about 10 nm width). Due to the difference of the wavelength width therebetween, typically, measured spectral data for light having a narrower range is estimated based on the RGB brightness values of the target area.

SUMMARY OF THE INVENTION

According to the above-referenced publication, a plurality of pieces of sample data, each of which includes RGB brightness values, are obtained using the electronic endoscope and, at the same time, corresponding spectral characteristics are measured using the spectrometer. Then, a conversion matrix for obtaining the spectral characteristic based on the RGB brightness values is generated. Once the conversion matrix is generated, the spectral characteristic at a desired pixel of an image of the human cavity can be calculated from the RGB brightness values.

If the spectral characteristics of a target portion are closely related to the spectral characteristic of the samples, the spectral characteristic of the target portion can be evaluated relatively accurately with use of the conversion matrix. If the spectral characteristics of the target portion is different from the samples used for generating the conversion matrix, the decree of precision of the evaluation of the spectral characteristics is relatively low.

In consideration of the above problem, the present invention is advantageous in that improved spectral characteristic calculating device and method are provided.

According to an aspect of the invention, there is provided a spectral characteristic calculation device that calculates spectral characteristic values based on brightness information at a pixel of a color image. The device includes a first storage that stores a plurality of conversion matrices, each of the plurality of conversion matrices being used to calculate the spectral characteristic values based on brightness values of a digital color image, a second storage that stores a plurality of pieces of brightness value information respectively corresponding to a plurality of sample groups each containing sample color image information, the plurality of conversion matrices being generated based on the sample color image information contained in the plurality of sample groups, respectively, an image receiving unit configured to receive digital color image data as target data, an evaluating unit configured to evaluate similarity of brightness value information of the target data with respect to each of the plurality of pieces of brightness value information of the plurality of sample groups, a selecting unit configured to select a conversion matrix corresponding to the sample group that is evaluated to have the highest similarity as the conversion matrix to be used for calculating the spectral characteristic, and a calculating unit configured to calculate the spectral characteristic values of the target data using the conversion matrix selected by the selecting unit.

Optionally, the evaluating unit may evaluate the similarity based on a Mahalanobis distance between the brightness information of the sample groups and the brightness information of the target data.

Further optionally, each piece of the brightness information may represent a ratio of the brightness of one of red, green and blue components to the brightness of another one of the red, green and blue components.

According to other aspects of the invention, there is provided a method of calculating a spectral characteristic at a pixel of a color image based on brightness values of the pixel. The method includes a step of preparing a plurality of conversion matrices, each of the plurality of conversion matrices being used to calculate the spectral characteristic based on a plurality of pieces of brightness value information respectively corresponding to a plurality of sample groups each containing sample color image information, the plurality of conversion matrices being generated based on the sample color image information contained in the plurality of sample groups, respectively, a step of receiving digital color image data as target data, a step of evaluating similarity of brightness value information of the target data with respect to each of the plurality of pieces of brightness value information of the plurality of sample groups, a step of selecting a conversion matrix corresponding to the sample group that is evaluated to have the highest similarity, and a step of calculating the spectral characteristic by converting the brightness value information of the target data using the conversion matrix selected by the selecting unit to the spectral characteristic values.

Optionally, the step of evaluating may evaluate the similarity based on a Mahalanobis distance between the brightness information of the sample groups and the brightness information of the target data.

Further optionally, each piece of the brightness information may represent a ratio of the brightness of one of red, green and blue components to the brightness of another one of the red, green and blue components.

BRIEF DESCRIPTION OF THE ACCOMPANYING DRAWINGS

DETAILED DESCRIPTION OF THE EMBODIMENTS

Hereinafter, referring to the accompanying drawings, a spectral characteristic calculation device according to an embodiment of the present invention will be described in detail.

Figure 1:
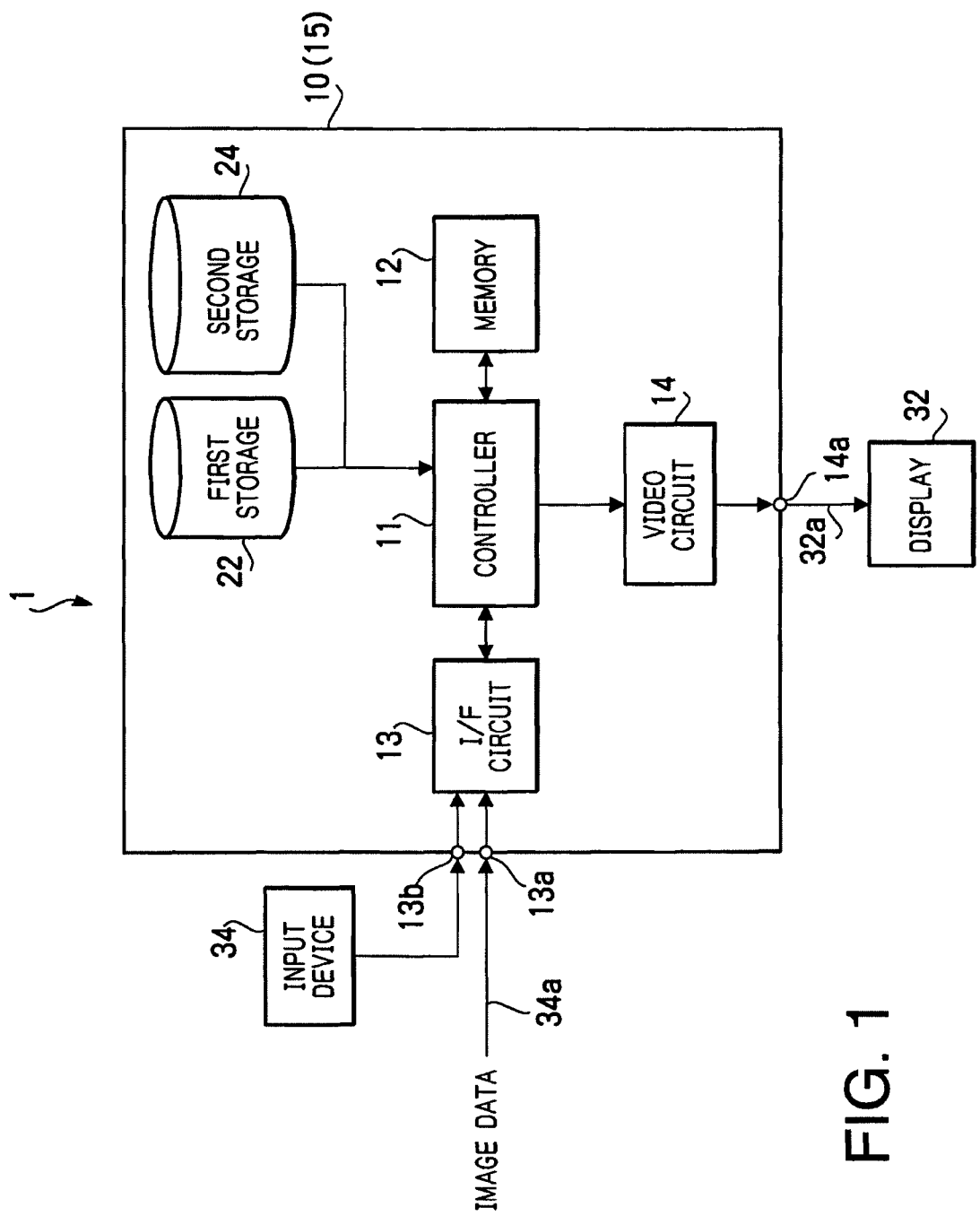
FIG. 1 is a block diagram showing a functional configuration of a spectral characteristic calculation device according to an embodiment of the invention.

FIG. 1 is a block diagram showing a functional configuration of a spectral characteristic calculation device 1 (hereinafter, simply referred to as a device 1) according to an embodiment of the invention. The device 1 is for calculating a spectral characteristic at a pixel of an image, which is captured with an imaging device such as an electronic endoscope, based on RGB (Red, Green and Blue) brightness information. Specifically, according to the embodiment, the device 1 calculates reflectivity for narrow wavelength widths. The narrow wavelength width is a range (width) of 1 nm-100 nm, and preferably, a range of 5 nm-10 nm.

As shown in FIG. 1, the device 1 includes a calculation unit 10, a display 32 connected with the calculation unit 10, and an input unit 34 including a keyboard and a mouse.

The calculation unit 10 is provided with a case 15 accommodating a controller 11, a memory 12, an interface 13, a video circuit 14, a first storage 22 and a second storage 24.

The display 32 is connected to the video circuit 14 via a connection port 14a provided on an outer surface of the case 15 and a cable 32a. The controller 11 controls the video circuit 14 so that an image is displayed on the display 32.

The interface 13 is, for example, a USB (Universal Serial Bus) host adapter circuit, to which the input unit 34 and/or an external memory storing image data to be processed by the device 1 can be connected via a port 13a and a cable 34a.

The first storage 22 and the second storage 24 store an RGB data group and a conversion matrix group, respectively. The controller 11 calculates the spectral characteristics of an pixel of the image data which is input through the interface 13 based on the RGB data group and the conversion matrix group respectively stored in the first storage 22 and the second storage 24.

Hereinafter, a process for calculating a spectral characteristic of a desired pixel of the input image will be described.

Figure 2:
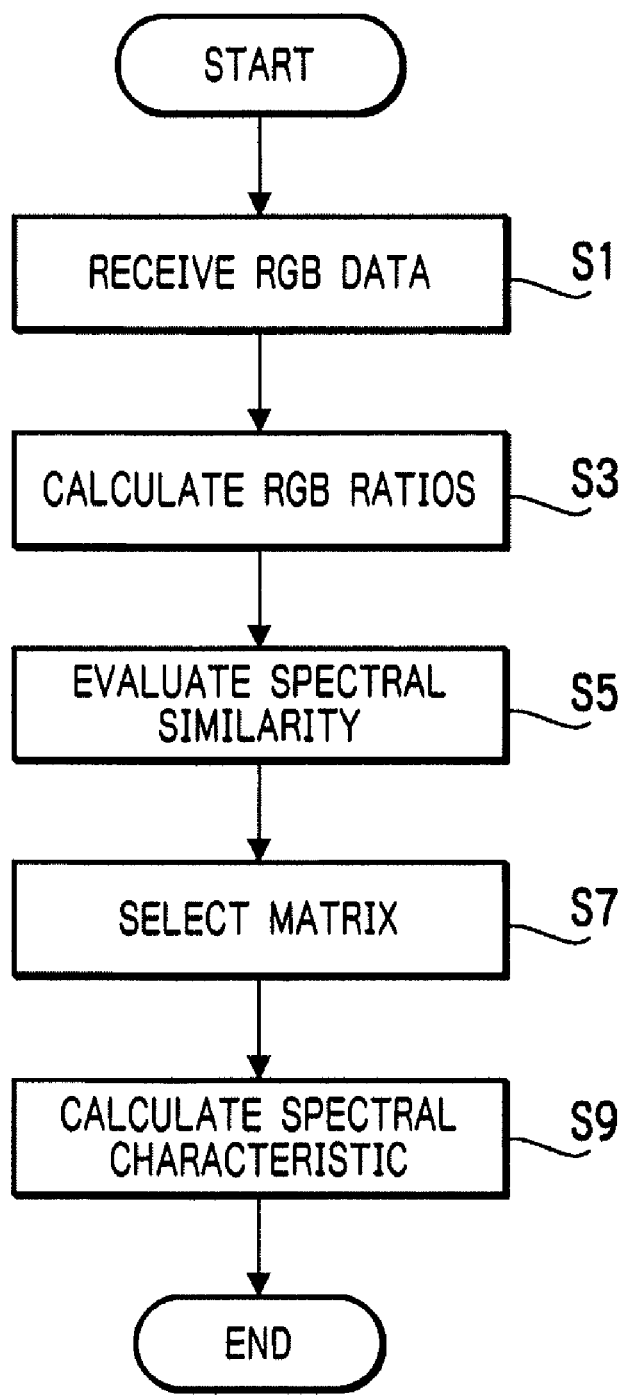
FIG. 2 shows a flowchart illustrating a calculation process according to the embodiment of the invention.

FIG. 2 shows a flowchart illustrating a calculating process which is executed by the controller 11.

In S1, the controller 11 receives RGB data of a desired pixel of the input image via the interface 13. Then, in S3, the controller 11 calculates a ratio of an amplitude of an R (red) component to an amplitude of a G (green) component, and a ratio of an amplitude of a B (blue) component to an amplitude of the G (green) component of the received RGB data. Then, in S5, the controller 11 evaluates the thus calculated ratios and selects, from the first storage 22, RGB data exhibiting spectral similarity to the desired pixel. Then, in S7, the controller 11 selects, from the second storage 24, a matrix corresponding to the RGB data determined to exhibit the spectral similarity to the desired pixel. Then, in S9, the controller 11 calculates the spectral characteristic using the conversion matrix determined to be used in S7.

Hereinafter, the above process will be described in detail. According to the embodiment, an appropriate one of a plurality of conversion matrices stored in the second storage 24 is selected, and a product, which represents the spectral characteristic, of matrices is calculated based on the RGB brightness values and the selected conversion matrix. Specifically, according to the embodiment, a wavelength range from 300 nm-700 nm, corresponding to a visible radiation, is divided into 10 nm width, and a reflectivity of each divided wavelength width is obtained. In the following description, the reflectivity of each wavelength width is represented by Ok (k=300, 310, 320, . . . , 700), where k is an integer representing a central wavelength of each wavelength width. For example, $O_{300}$ represents a reflectivity of light whose wavelength range is 295 nm-305 nm. It should be noted that the spectral characteristic O is represented by a matrix $(O_{300}, O_{310}, \ldots O_{700})$.

When the RGB brightness information b is represented by a matrix $(b_R, b_G, b_B)$, the spectral characteristic O is calculated using conversion matrix G and RGB brightness information b as follows.

$$\begin{bmatrix} o_{300} \\ o_{310} \\ o_{320} \\ \vdots \\ o_{700} \end{bmatrix} = \begin{bmatrix} G_{R-300} & G_{G-300} & G_{B-300} \\ G_{R-310} & G_{G-310} & G_{B-310} \\ G_{R-320} & G_{G-320} & G_{B-320} \\ \vdots & \vdots & \vdots \\ G_{R-700} & G_{G-700} & G_{B-700} \end{bmatrix} \begin{bmatrix} b_R \\ b_G \\ b_B \end{bmatrix} \quad (1)$$

The conversion matrix G is obtained as follows. A spectral characteristic $O_{Ref}$ of a sample is measured using a spectrometer. At the same time, RGB brightness values $b_{Ref}$ of the sample are obtained using an electronic endoscope or the like. The above measurement is performed for a plurality of samples (more than 100 samples) to obtain a plurality of sets of the spectral characteristics $O_{Ref}$ and associating RGB brightness values $b_{Ref}$. Then, an appropriate conversion matrix G for the sample is calculated in accordance with a least-square method.

According to the embodiment, N conversion matrices Gn (n=1, 2, 3, . . . , N) are stored in the second storage 24. Each of the conversion matrices Gn is calculated from the groups of the spectral characteristic $O_{Ref}$ and RGB brightness value $b_{Ref}$ of different samples. The groups of the samples used for calculating one conversion matrix Gn exhibit a similar tendency in terms of conversion from the brightness values to the spectral characteristics. That is, one conversion matrix Gn is calculated based on the sample group in which the wavelength ranges corresponding to the peak value of the reflectivity The RGB brightness values $b_{Ref}$ of the sample group used for obtain respective conversion matrices Gn will be used in an optimum matrix selecting process, which will be described later. Specifically, ratios of R brightness values to G brightness values ($r_{nR-k}$) and B rightness values to G brightness values ($r_{nB-k}$) are calculated. Then, the thus calculated ratios are categorized by each conversion matrix Gn to obtain the brightness value ratio group $r_{n-k}$ ($r_{nR-k}, r_{nB-k}$). In the above expressions, k=1, 2, 3, . . . , kmax. It is noted that kmax represents the number of the samples used for obtaining the conversion matrices Gn. Therefore, the value $k_{max}$ may be different for different sample group. The brightness value ratio group $r_{n-k}$ is stored in the first storage 22.

As described above, according to the embodiment, there are N conversion matrices for calculating the spectral characteristics O from the RGB brightness values b. Therefore, before calculating the spectral characteristics, an optimum conversion matrix should be selected by executing the optimum matrix selection process.

According to the embodiment, the sample group which has the most similar tendency with respect to the RGB brightness values bi is selected using a Maharanobis distance. That is, Maharanobis distances Dn are calculated for the brightness value ratios ri based on a formula below and selects one conversion matrix Gn which is obtained from the sample group for which the Maharanobis distance Dn has the smallest value.

$$D_n = \sqrt{\begin{bmatrix}(r_{iR} - E(r_{nR-k})) \\ (r_{iB} - E(r_{nB-k}))\end{bmatrix} \cdot S_n^{-1} \cdot [(r_{iR} - E(r_{nR-k}))(r_{iB} - E(r_{nB-k}))]} \quad (2)$$

In formula (2), a function E(x) represents an average of x. Therefore, $E(r_{nR-k})$ and $E(r_{nB-k})$ are calculated in accordance with the following equations.

$$E(r_{nR-k}) = \frac{1}{k\max}\sum_{k=1}^{k\max}(r_{nR-k})$$

$$E(r_{nB-k}) = \frac{1}{k\max}\sum_{k=1}^{k\max}(r_{nB-k})$$

Further, a function $S_n^{-1}$ in formula (2) represents an inverse matrix of a covariance matrix Sn with respect to the brightness value ratio group $r_{n-k}$. The covariance matrix $S_n$ is calculated in accordance with an equation below.

$$S_n = \begin{bmatrix} (E(r_{nR-k} - E(r_{nR-k}))^2) & (E((r_{nR-k} - E(r_{nR-k}))(r_{nB-k} - E(r_{nB-k})))) \\ \begin{pmatrix}E((r_{nR-k} - E(r_{nR-k})) \\ (r_{nB-k} - E(r_{nB-k})))\end{pmatrix} & (E(r_{nB-k} - E(r_{nB-k}))^2) \end{bmatrix}$$

Using formula (2), the Mahalanobis distances Dn are calculated for all the sample groups. Then, the smallest one of the thus calculated Mahalanobis distances Dn is selected. Then, the conversion matrix Gn corresponding to the selected distance Dn is selected, and the spectral characteristic O is calculated based on the RGB brightness values bi of a pixel of the image data using formula (1). It should be noted that the smaller the Mahalanobis distance Dn is, the higher the similarity is between the brightness value ratios $r_i$ of the input image data and the brightness value ratios $r_{n-k}$ of the sample group. Therefore, by selecting the conversion matrix Gn obtained from the sample group of which the Mahalanobis distance Dn has the smallest value, the spectral characteristic O can be calculated with a higher accuracy.

The present disclosure relates to the subject matter contained in Japanese Patent Application No. P2008-097810, filed on Apr. 4, 2008, the subject matter of which is expressly incorporated herein by reference in its entirety.

What is claimed is:

1. A spectral characteristic calculation device that calculates spectral characteristic values, comprising:
   a first storage that stores brightness value information for each of a plurality of sample groups, each of the plurality of sample groups containing sample color image information;
   a second storage that stores a plurality of conversion matrices, each of the plurality of conversion matrices being generated based on the sample color image information contained in one of the plurality of sample groups;
   an image receiver that receives digital color image data as target data; and
   a controller that receives the target data received by the image receiver, accesses the brightness value information for each of the plurality of sample groups stored in the first storage, accesses the plurality of conversion matrices stored in the second storage, and further:
      evaluates a similarity of brightness value information of the target data with respect to the brightness value information of each of the plurality of sample groups;
      selects a conversion matrix of the plurality of conversion matrices that corresponds to one of the plurality of sample groups that is evaluated to have a highest similarity; and
      calculates the spectral characteristic values of the target data based on the conversion matrix selected by the selector.

2. The spectral characteristic calculating device according to claim 1,
   wherein the controller evaluates the similarity based on a Mahalanobis distance between the brightness value information of each of the plurality of sample groups and the brightness value information of the target data.

3. The spectral characteristic calculating device according to claim 1,
   wherein the brightness value information of each of the plurality of sample groups and the target data represents a ratio of brightness of one of a red component, a green component, and a blue component to the brightness of an other one of the red component, the green component, and the blue component.

4. A method of calculating a spectral characteristic at a pixel of a color image, the method utilizing a first storage and a second storage, the first storage storing brightness value information for each of a plurality of sample groups, the second storage storing a plurality of conversion matrices respectively corresponding to the plurality of sample groups, the method comprising:
   receiving digital color image data as target data;
   accessing, by a controller, the target data, the brightness value information for each of the plurality of sample groups stored in the first storage, and the plurality of conversion matrices stored in the second storage;
   evaluating, by the controller, a similarity of brightness value information of the target data with respect to the brightness value information of each of the plurality of sample groups;
   selecting, by the controller, a conversion matrix of the plurality of conversion matrices that corresponds to one of the plurality of sample groups that is evaluated to have a highest similarity; and
   calculating, by the controller, the spectral characteristic by converting the brightness value information of the target data, using the selected conversion matrix, to spectral characteristic values.

5. The method according to claim 4,
   wherein the similarity is evaluated based on a Mahalanobis distance between the brightness value information of each of the plurality of sample groups and the brightness value information of the target data.

6. The method according to claim 4,
wherein the brightness value information of each of the plurality of sample groups and the target data represents a ratio of brightness of one of a red component, a green component, and a blue component to the brightness of an other one of the red component, the green component, and the blue component.

* * * * *